Figure 1:
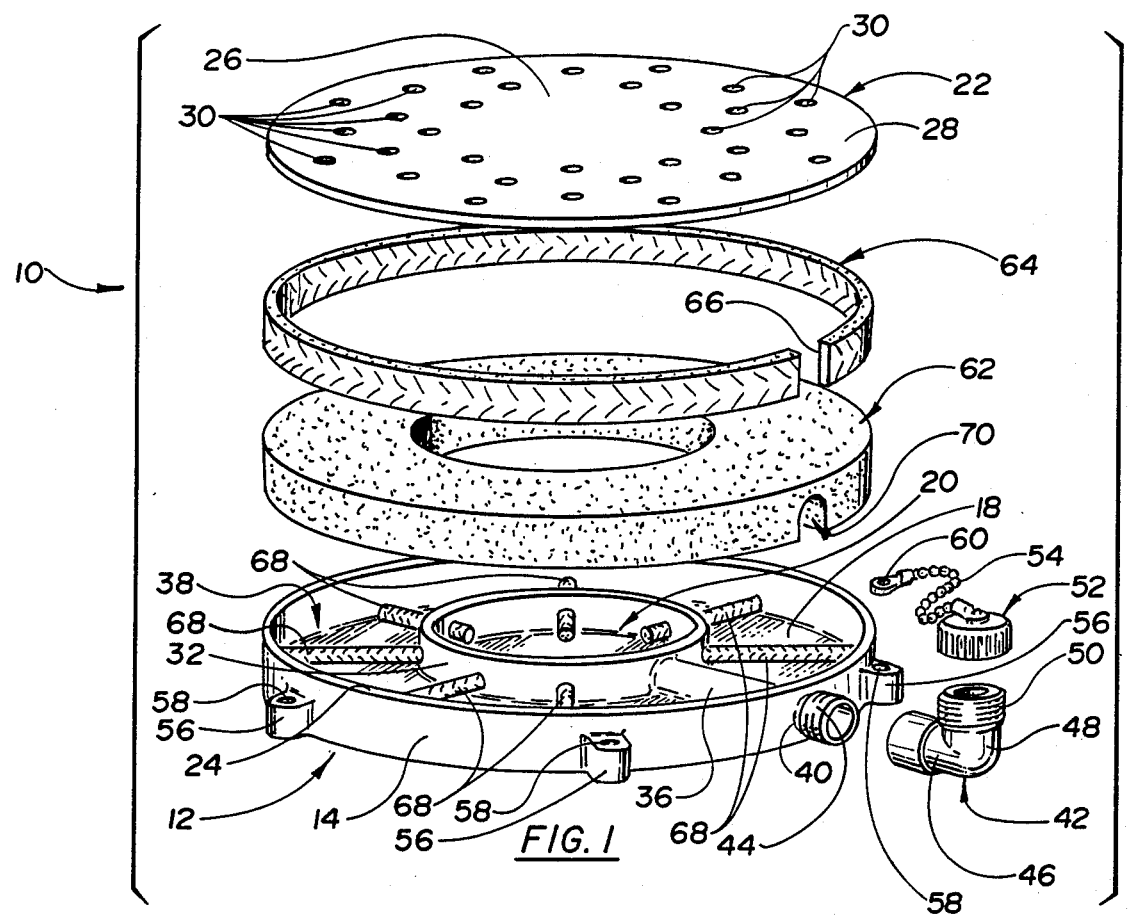

United States Patent [19]
Hoffman

[11] Patent Number: 4,890,791
[45] Date of Patent: Jan. 2, 1990

[54] DEVICE FOR ELIMINATING MALODOROUS SMELLS

[76] Inventor: Craig O. Hoffman, 10364 Newport Dr., Eden Prairie, Minn. 55344

[21] Appl. No.: 252,258

[22] Filed: Sep. 30, 1988

[51] Int. Cl.$^4$ .............................................. A61L 9/12
[52] U.S. Cl. ........................................ 239/44; 239/57; 239/326
[58] Field of Search ................... 239/34, 44, 45, 51.5, 239/57, 326

[56] References Cited

U.S. PATENT DOCUMENTS

| | | | |
|---|---|---|---|
| 562,495 | 6/1896 | Sidway | 239/45 |
| 4,327,056 | 4/1982 | Gaiser | 239/51.5 |
| 4,428,892 | 1/1984 | Berliner | 239/51.5 |

Primary Examiner—Robert J. Oberleitner
Assistant Examiner—Karen B. Merritt
Attorney, Agent, or Firm—Lawrence M. Nawrocki

[57] ABSTRACT

A device (10) for use in eliminating malodorous smells from a confined area. The device (10) includes a housing (12) defined by a side-wall (14) and walls (18, 22) closing opposite axial ends (16, 24) thereof. A reservoir (20) is defined within the housing (12) within an annular, interior wall (32). An annular space (38) is defined, thereby, between the interior wall (32) and the side-wall (14) of the housing (12). A porous insert (62) formed of fibrous material is received within the annular space (38). An annular ring of wicking material (64) encircles the insert (62), and a plurality of angularly-spaced, radially-extending spoke-like wicks (68) extend from the reservoir (20) to the ring wicking material (64). Liquid neutralizing agent (34) in the reservoir (20) is conducted from the reservoir (20), through the spoke-like wicks (68) to the ring wicking material (64), and, in turn, to the porous insert (62).

4 Claims, 1 Drawing Sheet

U.S. Patent

Jan. 2, 1990

4,890,791

DEVICE FOR ELIMINATING MALODOROUS SMELLS

TECHNICAL FIELD

The present invention deals broadly with the field of the elimination of odors in areas where malodorous smells exist. The invention is related to a technology for the elimination of such smells particularly in enclosed areas. More specifically, the invention focuses upon structures for the storage and delivery of a liquid chemical agent which operates upon the odors. The particular structure of the preferred embodiment of the present invention is intended for use particularly with a liquid neutralizing agent, rather than a masking agent.

BACKGROUND OF THE INVENTION

Malodorous smells exist in many environments. Such odors are created in industrial, commercial, and residential environments. In industrial environments, the odors are often created by the practicing of processes involving the use of pungent chemicals. In commercial and residential environments malodorous smells can be generated by, for example, cigarette smoking.

Waste product odors can exist in all environments. Trash receptacles are, typically, fraught with odors from buteric acid, ammonia, mercaptain, and hydrogen sulfide.

Certainly, attempts have been made to eliminate or minimize the effects of such odors. One offered solution has been to provide a cartridge having a solid pellet carried therein. The cartridge can be mounted at an appropriate location in a waste basket, garbage can, dumpster, or even a water closet. As the pellet functions to deodorize the area where it has been placed, the pellet sublimes. As sublimation occurs, the pellet becomes depleted.

In some devices known in the prior art, a pellet can be replaced. Such replacement can, typically, be effected only after complete depletion of a pellet, however, in view of the solid nature of the pellet and the limited space available in the carrying cartridge for pellet reception. Consequently, there is, typically, a period of time when no deodorizer is in the cartridge, and odor regeneration occurs during that interim.

In other attempted solutions, liquid agents have been employed. When using a liquid or other fluid agent, however, the cartridge is expendable, and, once the agent becomes depleted, the cartridge is discarded. Again, therefore, there is a period of time, typically, when elimination of odors does not occur, and during which odor regeneration proceeds.

A number of types of agents for odor treatment are utilized. Broadly, such agents fall into two categories. These include neutralizers and maskers. The latter category is one wherein an attractive odor is disbursed throughout the air to "supersede" the malodorous smell sought to be eliminated. While devices employing such agents, in some instances, improve the situation, there is, typically, an undertone of the repulsive smell. Even when the masking agent is of a nature to generate a counter-odor sufficiently strong so that an extremely faint remnant of the repulsive odor exists, or no remnant of the repulsive odor exists, the smell generated by the agent can become overpowering and unacceptable in itself.

Odor neutralizing agents, on the other hand, function to interact with the obnoxious odors and chemically neutralize them. Currently, there is only one product on the market, of which Applicant is aware, that is a non-toxic liquid having no adverse effects on a handler of the liquid, even under the most unfavorable circumstances, is non-flammable, is non-explosive, is non-corrosive, and functions well to neutralize buteric acid, ammonia, mercaptain, and hydrogen sulfide smells. That product is a liquid agent marketed under the trademark "X-O" by the X-O Corporation of Dallas, Tex.

Even with this particular agent, however, problems as articulated heretofore exist. That is, there is no completely adequate delivery system for disbursing the agent so that it can optimally function to accomplish its intended goals.

The present invention includes improved apparatus for delivering such an agent to neutralize malodorous smells. It functions to overcome problems and incorporate desired characteristics dictated by the prior art.

SUMMARY OF THE INVENTION

The present invention is a device which distributes a liquid neutralizing agent throughout the device so that the agent is exposed to the air in an area from which it is desirable to eliminate malodorous smells. The device is intended for use in a confined area such as a dumpster or garbage can, although it certainly has a broader application. The device includes a housing which has one or more air flow ports formed therein. The housing encloses a porous material insert, and it confines that insert so that air flow passing through the housing through the one or more ports formed therein will sinuously pass throughout the fibers of the insert. The fibrous structure of the insert is such so as to facilitate dispersal of the liquid neutralizing agent throughout the insert. As a result, the air passing through the insert will have a maximum interface with the agent. The device also includes an enclosure which defines a reservoir. The enclosure is structured so that, as liquid neutralizing agent filling the reservoir is depleted, replenishment can be effected. The device also includes means for conducting liquid neutralizing agent in the reservoir to various locations about the insert so that maximum distribution of the agent throughout the insert can be accomplished.

In a preferred embodiment of the invention, the housing is circularly cylindrical in construction. An interior annular wall, concentric and radially aligned with an annular side-wall of the housing, defines an interior reservoir.

In that embodiment, the porous material insert is also annular, the insert having an inside diameter closely approximating the outside diameter of the interior wall within the housing. The outside diameter of the insert is slightly smaller than the inside diameter of the annular side-wall of the housing. Consequently, an annular ring of wicking material can be interposed between the insert and the annular side-wall of the housing in engagement with the insert.

A plurality of spoke-like wicking elements, in that embodiment, extend from the reservoir to the annular ring of wicking material. With such a structure, the liquid agent in the reservoir is conducted through the spoke-like elements and to the annular ring of wicking material.

Because of radial alignment of the annular wick with the interior wall enclosing the reservoir, the spoke-like elements, it is intended, extend through space occupied by the porous material insert. As the liquid neutralizing agent is drawn through the various wicking components, therefore, the agent will be distributed to numerous locations about the insert so that maximum dispersal of the agent is accomplished.

Means can be provided for selectively replenishing the radially central reservoir formed in the device with the liquid agent, as that agent becomes low. A threaded feed neck can be carried by the annular side-wall of the housing, the feed neck communicating, through a filling duct passing radially through the space occupied by the porous material insert, with the interiorly disposed reservior. An angled elbow can be mated to the feed neck to facilitate filling. A cap can be threaded on to the end of the angled fitting remote from the feed neck to preclude leakage of the liquid neutralizing agent from the reservoir during placement and operation of the apparatus.

The present invention is thus an improved device for eliminating malodorous smells in a confined area such as a garbage pail or dumpster. More specific features and advantages obtained in view of those features will become apparent with reference to the DETAILED DESCRIPTION OF THE INVENTION, appended claims, and accompanying drawing figures.

BRIEF DESCRIPTION OF THE DRAWING

FIG. 1 is an exploded perspective view of a device in accordance with the present invention; and FIG. 2 is a side sectional view of the device in FIG. 1.

DETAILED DESCRIPTION OF THE INVENTION

Referring now to the drawing wherein like reference numerals denote like elements throughout the several views, FIG. 1 illustrates, in an exploded portrayal, a device 10 in accordance with the present invention. The device 10 includes a housing which is, in the embodiment illustrated in the figures, generally circularly cylindrical in configuration. An annular side-wall 14 gives cylindrical form to the housing 12, and a first axial end 16 of the housing 12 is closed in some manner.

While it would be possible to have a surface in the space in which the device 10 is to be mounted serve to close the first axial end 16, more typically, a continuous disk-like wall 18 would permanently close the first axial end 16. This is so, since, if the surface to which the device 10 is to be mounted served to close the housing 12, some sort of seal would have to be provided to preclude leakage of a liquid neutralizing agent received in a radially inwardly disposed reservoir 20.

A disk-like cover 22, similar to that which might close the first axial end 16 of the housing 12 is provided to close the second axial end 24 thereof. This cover 22, or circular wall, has a central portion 26 which is unperforated. There is, however, an annular portion 28 disposed radially outward from the unperforated portion 26, which has a plurality of perforations 30 provided therein.

An annular interior wall 32 is provided within the housing 12. This wall 32 is generally concentric and radially aligned with the annular side-wall 14 of the housing 12. Additionally, it extends from the first axial end 16 of the housing 12 to the cover or wall 22 closing the second axial end 24 of the housing 12. The reservoir 20 is defined within annular wall 32.

The interior annular wall 32 has a diameter so that, when the cover 22 is fitted to the housing's side-wall 14, the reservoir 20 enclosed by the interior wall 32 will not communicate with the outside of the housing 12 through the perforations 30 provided in the annular portion 28 of the cover 22. That is, the radially innermost perforations 30 in the cover 22 would be disposed radially outwardly from the interior wall 32. As a result, as previously indicated, the unperforated portion 26 of the cover 22, together with the interior wall 32 and any wall closing the first axial end 16 of the housing 12, defines the reservoir 20 for receiving and distributing a liquid neutralizing agent 34.

When the housing 12 is assembled and the device 10 is mounted at a location for operation, the reservoir 20 can be filled through a filling duct 36 passing radially inwardly from the annular side-wall 14 of the housing 12, through an annular space 38 between that wall 14 and the annular, interior wall 32, and through the interior wall 32. The filling duct 36 can be provided with a feed neck 40 extension external to the annular side-wall 14 of the housing 12.

To facilitate filling, an angled elbow fitting 42 can be mated to the feed neck 40. Mating can be accomplished, by, for example, providing external threads 44 on the feed neck 40 which are compatible with internal threads (not shown) within a first arm 46 of the elbow fitting 42. The other arm 48 of the fitting 42 can be provided with threads, as at 50, to receive a closure cap 52.

In some embodiments, such an elbow fitting 42 and closure cap 52 can comprise integral parts of the device 10. When such is the case, a beaded chain 54, secured at one end thereof to the closure cap 52, can be attached, at its other end, to the housing 12. This can be accomplished in a manner as will be described hereinafter.

Mounting of the housing 12 at its desired location can be accomplished in any appropriate manner. The figures illustrate a housing side-wall 14 which is made with integrally formed extrusions 56, angularly spaced about the periphery of the side-wall 14, formed therein. Apertures 58 are provided in these extrusions 56, and corresponding apertures (not shown) in the mounting wall, provided at locations wherein each of the apertures 58 in the extrusions 56 can be registered with an associated aperture in the mounting wall, can be formed in the mounting wall. Screws or bolt/nut arrangements (not shown) can be employed, therefore, for mounting, either the screws or bolts being passed through the apertures 58 in the extrusions 56 and into the apertures in the mounting wall.

When the device 10 is mounted in this manner, the screw or bolt can be employed to attach the elbow fitting closure cap 52. A screw or bolt can be passed through an eyelet 60 at an end of the chain 54 remote from the end at which it is attached to the cap 52.

It will be understood, however, that the means described above for mounting the device 10 is not exclusive. It is also envisioned that hook/pile material or some sort of adhesive tape could also be utilized.

A porous material insert 62 is interposed in the annular space 38 defined between the interior annular wall 32 and the housing's side-wall 14. It is envisioned that the radial dimension of this annular insert 62 would approximate the radial dimension of the annular space 38 in which it is received.

While the inner diameter of the insert 62 is substantially the same as the outer diameter of the interior wall 32, the outer diameter of the insert 62 is somewhat smaller than the inner diameter of the housing side-wall closure 14. As a result, an annular ring of wicking material 64 can be received between the insert 62 and the housing's side-wall 14.

As shown in FIG. 1, the ring of wicking material 64 can be split at a point about its periphery, as at 66. If desired, however, it can be a continuous ring specially sized to be fitted in the radial location described herein.

The figures also illustrate a plurality of radially-extending, angularly-spaced wicking elements 68. While FIG. 1 illustrates seven of such elements 68 angularly-spaced, along with the filling duct 36, at 45° from one another, lesser or greater numbers of such elements 68 could be employed, and they could be disposed relative to each other at different angular spacings.

Figure 2:
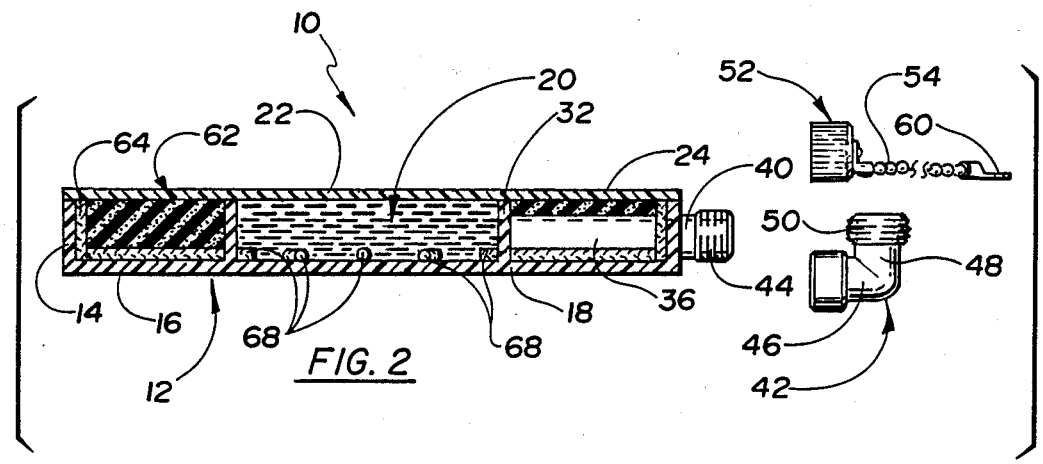

As seen best in FIG. 2, these elements 68 can be made to extend adjacent the wall 18 closing the first axial end 16 of the housing 12. Each wicking element 68 has a first end disposed within the reservoir 20 defined with the interior annular wall 32, and a second end extending to the ring of wicking material 64. As will be able to be seen in view of this disclosure, these radially-extending wicking elements 68 traverse the annular space 38 defined between the interior annular wall 32 and the housing's side closure wall 14.

In view of the fact that these elements 68 can be made adjacent the wall 18 closing the first axial end 16 of the housing 12, minimal obstruction to placement of the porous material insert 62 will result. In any case, however, the insert 62 is deformable to some extent and is able, therefore, to accommodate the wicking elements 68.

If desired, a recess 70 can be specifically provided in the insert 62 to accommodate the run of the filling duct 36. As seen in FIG. 1, scalloped recess 70 can be provided for such a purpose.

Both the radially-extending, spoke-like wicking elements 68 and the annular ring of wicking material 64 can be formed of any appropriate material. Typically, braided cotton, such as is used in kerosene lanterns, would be employed. What is desirable, however, is that, regardless of what material is used, it will adequately convey the liquid neutralizing agent 34 from the reservoir 20, through the spoke-like wicking elements 68, and to and throughout the annular ring of wicking material 64.

The porous material insert 62 would be formed of any appropriate mesh-like material. It is envisioned that the insert 62 would be relatively coarse. By providing such a coarse material, a number of advantages could be achieved. First, the liquid agent 34 conveyed throughout the wicking material 64, 68 could flow from the wicking material 64, 68 and throughout the mesh mass more easily. Further, however, where the fibers are spaced at greater distances from one another, air flow around the fibers is maximized. As a result, more efficient functioning of the device 10 will result.

In use, the housing 12 is mounted to, for example, the lid of a garbage can (not shown) by employment of the intended mounting means. A liquid neutralizing agent 34 is inserted into the reservoir 20 by mating a nipple of the agent bottle (not shown) to the angled elbow fitting 42. The agent 34 can, thereafter, be squirted from the bottle, through the fitting 42, along the filling duct 36, and into the reservoir 20. The elbow fitting 42 would then be closed by the closure cap 52 so that no leakage would occur.

Air in the garbage pail, to whose lid the device housing 12 were attached, would, thereafter, pass through the apertures 30 in the housing cover 22, around the fibers of the porous material insert 62, and out of the housing 12 again, through the perforations 30. The liquid agent 34, having been inserted into the reservoir 20, will have passed through the spoke-like wicking elements 68 to the annular ring of wicking material 64 and, in turn, along the fibers of the porous material insert 62. As the air having entered the device housing 12 passes around the fibers along which the neutralizing agent 34 has flowed, a chemical "scrubbing" effect will occur. As a result, the malodorous smells will not be merely masked, but, rather, will be neutralized so that no odor, whatsoever, exists.

In order to accomplish this chemical scrubbing and odor neutralization, an appropriate neutralizing agent 34 would be selected for insertion into the reservoir 20. One such agent found to be particularly appropriate is marketed under the trademark "X-O". That product is sold by the X-O Corporation of Dallas, Tex.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. Apparatus for eliminating malodorous smells in a confined area by distributing a liquid neutralizing agent for exposure to the air in the area, comprising:
    (a) a circular housing having at least one air flow port formed therein;
    (b) an annular, fibrous, porous material insert received within said housing so that air flow through said port will pass through said insert, the fibrous structure of said insert being such as to facilitate dispersal of liquid neutralizing agent coming in contact therewith throughout said insert;
    (c) an enclosure within said housing, defining a reservoir for receiving the liquid neutralizing agent, said reservoir being replenishable as liquid neutralizing agent therein becomes depleted; and
    (d) an annular ring of wicking material circumferentially enclosing said annular porous material insert, and a plurality of angularly-spaced, radial spokes of wicking material extending from said reservoir to said annular ring of wicking material.

2. Apparatus in accordance with claim 1 wherein said housing includes an annular wall engaging an inside diameter of said porous material insert, said enclosure defining said reservoir comprising said annular wall.

3. A cartridge for holding and distributing a liquid neutralizing agent to expose the agent to the air in a confined area permeated by malodorous smells, comprising:
    (a) a cylindrical housing having a first axial end for attachment to a surface in an area from which the malodorous smells are to be eliminated, a wall closing a second axial end of said housing, and an annular circumferential side-wall, said wall closing said second axial end of said housing having a plurality of perforations formed in an annular portion thereof radially outward from a central unperforated portion;

(b) an interior annular wall, radially coextensive with said annular side-wall of said housing and concentric therewith, said interior annular wall extending axially from said first axial end of said housing to said wall closing said second axial end of said housing, and being spaced radially inwardly from innermost perforations in said perforated portion of said wall closing said second axial end of said housing to define a reservoir replenishable as liquid neutralizing agent therein becomes depleted;

(c) a porous material insert received within said housing between said interior annular wall and said annular side-wall of said housing, and engaging said perforated portion of said wall closing said second axial end of said housing so that air flow through said perforations pass through said insert, said insert having a fibrous structure so as to facilitate dispersal of liquid neutralizing agent coming in contact with said insert therethroughout; and (d) means for conducting the liquid neutralizing agent from said reservoir to various locations about said insert.

4. Apparatus in accordance with claim 3 wherein said porous material insert is annular and has an inside diameter closely approximating an outside diameter of said interior annular wall, said conducting means including an annular ring of wicking material, circumferentially enclosing said annular porous material insert, and a plurality of angularly-spaced, radial spokes of wicking material extending from said reservoir to said annular ring of wicking material.

* * * * *